United States Patent
Bauer

[11] Patent Number: 5,916,175
[45] Date of Patent: Jun. 29, 1999

[54] BIOPSY NEEDLE APPLIANCE AND INSERTING GUIDE WITH ADJUSTABLE SAMPLE LENGTH AND/OR NEEDLE CUTTING STROKE

[75] Inventor: Alberto Bauer, Santo Domingo, Dominican Rep.

[73] Assignee: Allegiance Corporation, McGaw Park, Ill.

[21] Appl. No.: 08/781,779

[22] Filed: Jan. 9, 1997

[30] Foreign Application Priority Data

Jan. 26, 1996 [IT] Italy ................................ BO96A0034

[51] Int. Cl.$^6$ ........................................................ A61B 5/00
[52] U.S. Cl. ................................................................ 600/567
[58] Field of Search .................... 600/564–567; 606/167, 170

[56] References Cited

U.S. PATENT DOCUMENTS

| | | | |
|---|---|---|---|
| 4,958,625 | 9/1990 | Bates | 128/754 |
| 5,313,958 | 5/1994 | Bauer | 128/754 |
| 5,335,672 | 8/1994 | Bennet | 128/754 |

FOREIGN PATENT DOCUMENTS

| | | |
|---|---|---|
| 0 153 047 | 8/1985 | European Pat. Off. . |
| 0 429 390 | 5/1991 | Germany . |
| 92 00040 | 1/1992 | WIPO . |
| 95 13746 | 5/1995 | WIPO . |

*Primary Examiner*—Max Hindenburg
*Attorney, Agent, or Firm*—Kay H. P. Hannafan

[57] ABSTRACT

A system for tissue removal (biopsy) using a biopsy needle (2,3) appliance (30) and an inserting guide (20) extending lengthwise along a same (y) axis includes, between the handpiece-shell (1) and said inserting guide (20), adjusting means (4,5,6,7,8) adjustably mobile lengthwise suitable for moving said inserting guide (20) lengthwise with respect to said biopsy needle (2,3), so as front free end (22) of cannula-guide (20) may be adjustably positioned above or below front free end of cannula-cutting edge (3).

6 Claims, 2 Drawing Sheets

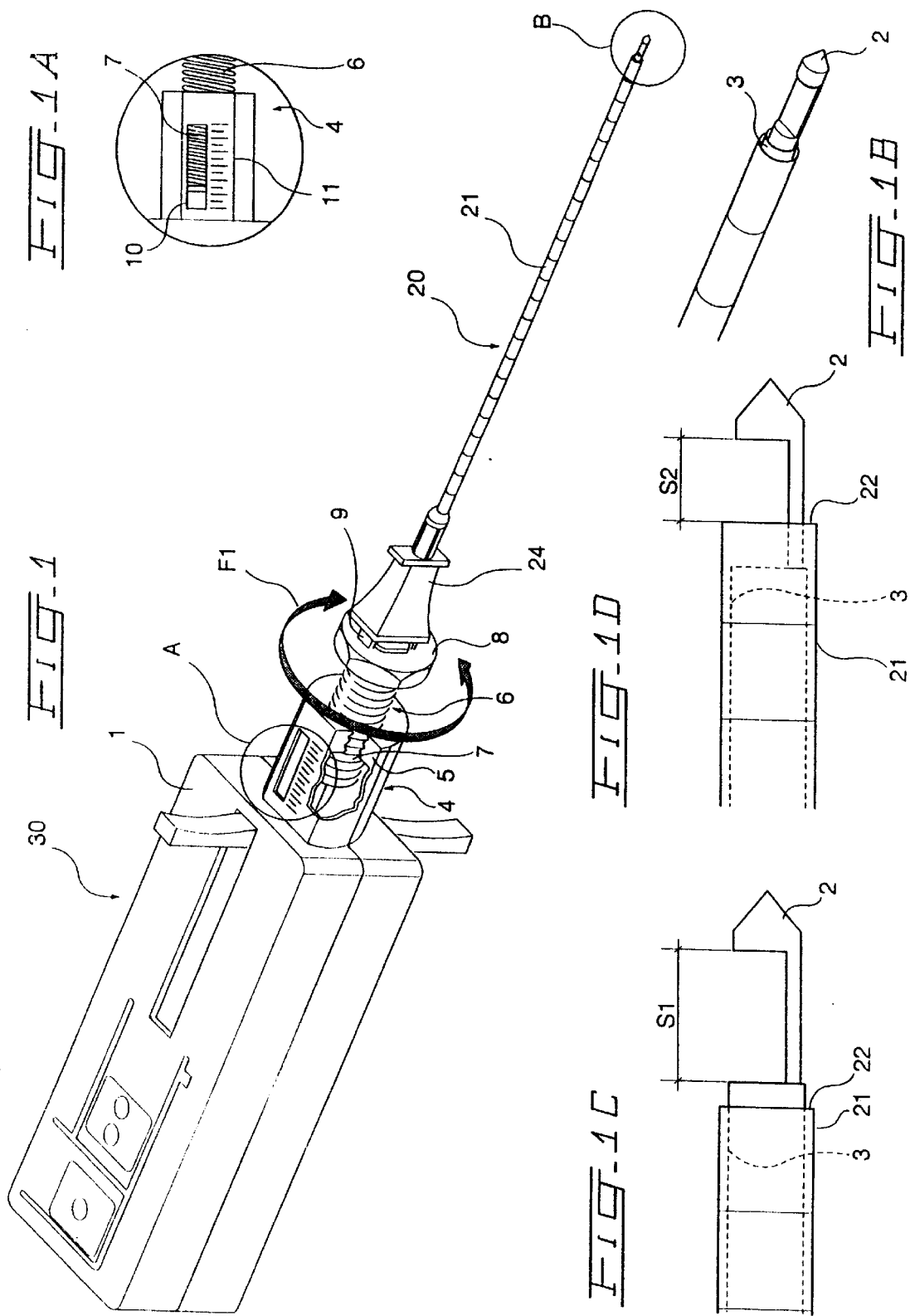

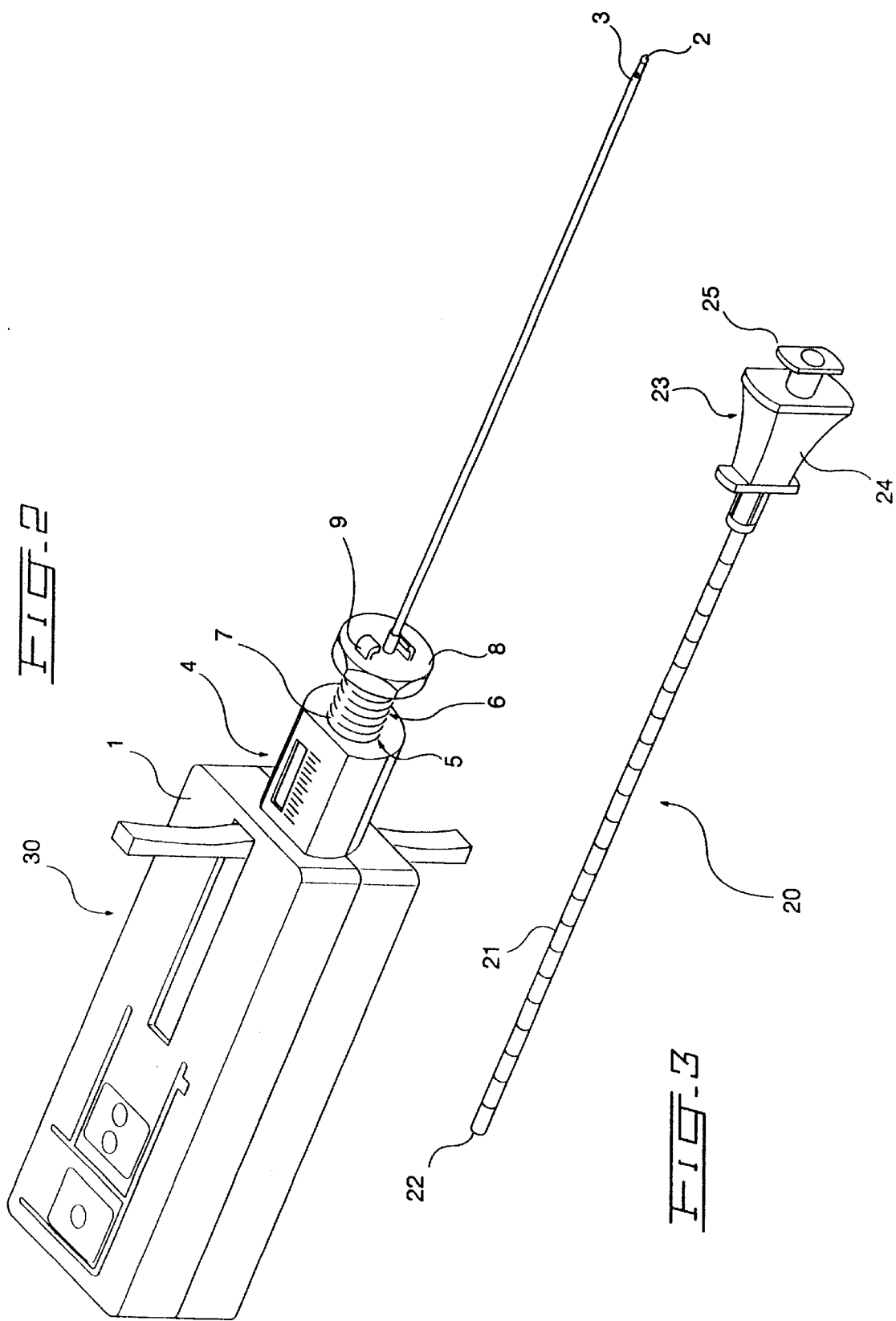

BIOPSY NEEDLE APPLIANCE AND INSERTING GUIDE WITH ADJUSTABLE SAMPLE LENGTH AND/OR NEEDLE CUTTING STROKE

FIELD OF THE INVENTION

The present invention relates to a system for tissue removal (biopsy) using a biopsy needle and an inserting guide with variable or adjustable sample length and/or needle cutting stroke.

DESCRIPTION OF THE PRIOR ART

At present biopsy needle appliances, see for instance U.S. Pat. No. 4,958,625, include a handpiece in which an operating device is contained which is suitable for actuating a biopsy needle which comes out of a front part of the handpiece. The biopsy needle includes a pointed stylet ending with a probe arranged coaxially in a cannula-cutting edge. A front part of the handpiece includes first hooking means capable of coupling with corresponding second hooking means carried by an inserting guide.

The inserting guide used in such systems includes, substantially, a cannula guide, made up of a hollow small tube, whose end opposite to the inserting/perforating end bears a trigger tang which is equipped with the second hooking means and a "luer" cone for a syringe in order to introduce a medicament for localized application after the tissue removal.

The operations for removal include, normally, trigger of the inserting guide on biopsy needle by hooking respective first and second hooking means one to the other so as to stiffen the resulting combination, which, so assembled, forms a perforating point which presents a stylet front point, cannula cutting edge front point, and cannula-guide front point.

After preparing the tool as mentioned above, the operating inserts the biopsy needle and cannula guide into the patent's body by positioning the needle front end into and/or in direction of the area which is the object of removal and, once the correct position is determined by magnetic resonance or CAT scanning or different systems, the operator actuates the stylet and cannula cutting edge in quick sequence to obtain the tissue sample.

Once the sampling has been performed, the mentioned first and second hooking means are released from one another and the biopsy needle is withdrawn from the inserting guide which remains in position to directly check the obtained sample.

Thus, should the sample turn out to be incorrect from the check which has been carried out, a new biopsy needle is inserted into the inserting guide to perform another sampling. Should the sample be correct, if necessary, a medicament is administered by applying a syringe to the "luer" cone and then the inserting guide is drawn out.

The above-mentioned system has the drawback that it does not allow variation and/or adjustment of sample length and/or needle cutting stroke, that is the stylet or cannula-cutting edge feed stroke beyond inserting guide free end.

Such a deficiency is particularly evident when tissue is to be removed in particular areas close to vitals or bones where, after positioning of the inserting guide or the biopsy needle set next to the area which is the object of removal (through magnetic resonance or CAT), it is necessary to vary and/or adjust feed stroke of stylet and cannula-cutting edge beyond cannula-guide free end, in order to avoid interfering with the vitals or bones.

OBJECT OF THE INVENTION

The object of this invention is to provide a system for tissue removal (biopsy) using a biopsy needle appliance and an inserting guide which is suitable for varying and/or adjusting sample length and/or cutting stroke of the needle.

SUMMARY OF THE INVENTION

According to the invention a system for tissue removal (biopsy) using a biopsy needle appliance and an inserting guide extending lengthwise along the same axis, comprises a shell-shaped handpiece containing a control device operating a biopsy needle. The biopsy needle extends out the front of the handpiece shell and including a perforating stylet and a cannula-cutting edge arranged coaxially suitable for being fed in rapid sequence to obtain a sample of tissue. The handpiece includes first hooking means frontally, and the inserting guide includes a cannula guide whose back portion opposite to the inserting portion includes second hooking means destined to couple with the first hooking means carried by the appliance. The system has, between the handpiece shell and the inserting guide, adjusting means movable adjustably lengthwise for moving the inserting guide lengthwise with respect to said biopsy needle so that the cannula-guide front free end may be adjustably positioned below or above the cannula-cutting edge front free end.

Through the use of this system it is possible to vary sample and/or biopsy needle cutting stroke length.

The advantages obtained by adopting this type of system are that one can perform removals with different lengths with the same appliance, and that one can vary and adjust biopsy needle cutting stroke length when the needle is inserted avoiding possible interference with vital parts.

BRIEF DESCRIPTION OF THE DRAWING

The above and other objects, features, and advantages will become more readily apparent from the following description, reference being made to the accompanying drawing in which:

FIG. 1 is a perspective view of the system of this intention;

FIG. 1A is a view of the detail A of FIG. 1;

FIG. 1B is a view of the detail B of FIG. 1;

FIG. 1C is a schematic view of detail B of FIG. 1 according to a first adjustment;

FIG. 1D is a schematic view of detail B of FIG. 1 according to a second adjustment;

FIG. 2 is a perspective view of the biopsy appliance; and

FIG. 3 is a perspective view of the inserting cannula.

DESCRIPTION OF THE PREFERRED EMBODIMENT

FIG. 1 shows a biopsy appliance 30, separately illustrated in FIG. 2, provided with an inserting guide 20, separately illustrated in FIG. 3.

Biopsy appliance 30 includes a handpiece or box 1 receiving a known biopsy needle operating device is placed, the biopsy needle being made up of a stylet 2 and a cannula cutting edge 3.

The handpiece 1 has a portion 4 on the front, equipped with a threaded hole 5 extending lengthwise, inside which back threaded part 7 of a spacing element 6 with a front head 8 whose front part is provided with first hooking means 9 is screwed.

Portion 4 of the handpiece 30 has a reading window 10 extending lengthwise, see also FIG. 1A, through which, by direct reading, it is possible to determine the longitudinal position of spacing element 6 with respect to portion 4, and to detect its longitudinal movements through a graduated scale 11.

Inserting guide 20, see FIG. 3, includes a cylindrical hollow cannula-guide 21, which presents a front end 22 and a back portion 23, where the latter carries a tang 24 which is equipped with second hooking means 25, the latter having a configuration allowing the hooking means to engage with hooking means 9 carried by head 8 of handpiece 1.

With this system, see FIG. 1, it is possible to vary the longitudinal position of inserting guide 20 with respect to biopsy appliance 30, by rotation of spacing element 6, as shown by the arrow F1.

FIG. 1C illustrates in schematic form the detail B of FIG. 1 in a first adjusting position to obtain a certain removal length removal. In this position, front end 22 of cannula guide 21 set back from the end of stylet 2 which has already been fed to perforate the tissue to be removed. In this condition it is evident that subsequent quick feed of cannula-cutting edge 2 will result in a sample having a length S1.

In case one wishes to reduce the length of sample and/or to reduce the cutting stroke, see FIG. 1D, by acting on spacing element 6, in one of the directions shown by arrow F1, it is possible to move spacing element 6 micrometrically and lengthwise, thus obtaining a longitudinal movement of inserting guide 20 with respect to appliance 30 and, for instance, to position the front end 22 of cannula guide 21 beyond the front end of the cannula cutting edge 3. With such a new adjustment, by advancing stylet 2 a sample with a length S2 less than the one mentioned above and a shorter cutting stroke will be obtained.

With this system the operator, by looking at window 10, will be able to determine before performing the removal operation the perforation stroke beyond front end 22 of the cannula guide of stylet 2 and cannula-cutting edge 3, as well as the removal length which will be obtained. Furthermore, the operator, by rotating element 6, will be able to vary the mentioned lengths and detect the adjustment through reading window 10.

The screw 7 spacing element 6 may be equally replaced by a different spacing element, for instance one of the snapping step-by-step type, without losing the inventive concept of this invention.

Description of the system for tissue removal (biopsy) described above is given as a non-restricted example and thus it is evident that any modification or variation may be made as suggested by practice or its use or employment and however within the scope of the following claims.

I claim:

1. A biopsy appliance comprising:
    a hand piece shell having an end, a biopsy stylet adapted to project beyond said end, a cannula coaxially surrounding said stylet and having a cutting edge at an end thereof remote from said hand piece shell cooperating with said stylet to remove a length of tissue in performing a biopsy, and operating means in said hand piece shell for actuating said cannula and said stylet by displacing said cannula and said stylet along a common axis into said tissue;
    a cannula guide coaxially surrounding said cannula and said stylet;
    first hooking means on said end of said hand piece shell and second hooking means on an end of said cannula guide proximal to said hand piece shell for coupling said cannula guide to said hand piece shell; and
    adjusting means between said first hooking means and said end of said hand piece shell for varying a spacing along said axis of said first hooking means from said hand piece shell, thereby enabling said cannula guide selectively to expose or cover said cutting edge.

2. The biopsy appliance defined in claim 1 wherein said adjusting means includes member formed on a front end thereof with said first hooking means and on a rear end thereof with means longitudinally adjustably engaged with said hand piece shell.

3. A biopsy appliance comprising:
    a hand piece shell having an end, a biopsy stylet adapted to project beyond said end, a cannula coaxially surrounding said stylet and having a cutting edge at an end thereof remote from said hand piece shell cooperating with said stylet to remove a length of tissue in performing a biopsy, and operating means in said hand piece shell for actuating said cannula and said stylet by displacing said cannula and said stylet along a common axis into said tissue;
    a cannula guide coaxially surrounding said cannula and said stylet;
    first hooking means on said end of said hand piece shell and second hooking means on an end of said cannula guide proximal to said hand piece shell for coupling said cannula guide to said hand piece shell; and
    adjusting means between said first hooking means and said end of said hand piece shell for varying a spacing along said axis of said first hooking means from said hand piece shell, thereby enabling said cannula guide selectively to expose or cover said cutting edge, said adjusting means comprising a longitudinal threaded hole formed in said hand piece shell and a spacer having a rear part threaded into said hole and a front part formed with said first hooking means.

4. The biopsy appliance defined in claim 3, further comprising indicator means for indicating position and longitudinal displacement of said cannula guide relative to said hand piece shell.

5. The biopsy appliance defined in claim 4 wherein said indicator means includes means for displaying relative positions of said spacer and said hand piece shell.

6. The biopsy appliance defined in claim 5 wherein said indicator means comprises a window extending longitudinally at said end of said hand piece shell and through which a position of said spacer is visible, and graduations along said window.

* * * * *